| United States Patent [19] | [11] Patent Number: 4,734,365 |
|---|---|
| Haga et al. | [45] Date of Patent: Mar. 29, 1988 |

[54] PROCESS FOR LIQUEFYING STARCH

[75] Inventors: Ryooichi Haga; Masahiko Ishida, both of Hitachi; Masako Katsurayama, Katsuta, all of Japan

[73] Assignee: Hitachi, Ltd., Tokyo, Japan

[21] Appl. No.: 795,779

[22] Filed: Nov. 7, 1985

[30] Foreign Application Priority Data

Nov. 9, 1984 [JP] Japan ................. 59-236916

[51] Int. Cl.$^4$ .............. C12P 19/14; C12N 9/28; C12R 1/145
[52] U.S. Cl. .................... 435/99; 435/202; 435/842
[58] Field of Search .............. 435/202, 99, 842

[56] References Cited

U.S. PATENT DOCUMENTS

| 4,284,722 | 8/1981 | Tamuri et al. | 435/94 |
|---|---|---|---|
| 4,578,352 | 3/1986 | Katkocin et al. | 435/99 |
| 4,600,693 | 7/1986 | Kindle et al. | 435/202 X |
| 4,613,570 | 9/1986 | Zeman | 435/99 |

Primary Examiner—Lionel M. Shapiro
Attorney, Agent, or Firm—Antonelli, Terry & Wands

[57] ABSTRACT

This invention relates to a process for liquefying starch. More particularly it relates to an appropriate process for liquefying starch by using a thermostable α-amylase which has an optimum working pH range in an acidic region and a low calcium requirement.

This invention provides a process for liquefying starch by using a calcium-requiring, thermostable α-amylase which requires a calcium concentration of 10 μm or below under a thermostable condition.

In the process of the present invention, it is unnecessary to add a calcium salt in liquefying starch and the starch slurry can be reacted while remaining acidic without neutralization, so that the load at the desalting step of the product can be significantly relieved.

6 Claims, 6 Drawing Figures

PROCESS FOR LIQUEFYING STARCH

BACKGROUND OF THE INVENTION

1. Field of the Invention

This invention relates to a process for liquefying starch. More particularly it relates to an appropriate process for liquefying starch by using a thermostable α-amylase which has an optimum working pH value in an acidic region and a low calcium requirement.

2. Description of the Prior Art

In order to prepare sweeteners such as glucose or isomerized sugars, starch is hydrolyzed with an α-amylase into dextrins which are further decomposed and/or isomerized with other enzymes such as glucoamylase and glucose isomerase. Furthermore α-amylases have been widely employed to desize fabrics. Recently mesophilic enzymes have been replaced by thermostable α-amylases. Thermostable enzymes are generally more stable to heating and pH changes than mesophilic enzymes so that the former are very useful in an enzymatic industry.

Conventional α-amylases are limited to those originating from aerobic bacterial (cf. Shimamura et al., Japanese Patent Publication No. 12946/1971, and L. L. Campbell et al., J. Biol. Chem., 236, 2952 (1961). Among these α-amylases, those originating from *Bacillus subtilis* and *Bacillus licheniformis* have been commercially produced and used in processing starch and desizing fabrics. These known α-amylases can not exhibit the thermostability with the protein of themselves until a calcium ion is added thereto. They require a calcium concentration of usually several mM to 20 mM (cf. Hattori, Japanese Patent Laid-Open No. 44652/1976 and No. 44690/1976) and at least 1 mM (cf. Saito, Japanese Patent Laid-Open No. 35083/1973). Thus the thermostability of conventional α-amylases would be significantly decreased at a calcium concentration of 1 mM or below or in the absence of calcium, as shown by the thermostability of an α-amylase originating from *B. licheniformis* (cf. Japanese Patent Laid-Open No. 12946/1971 and No. 35083/1973). Therefore a very low calcium concentration (100 μM or below) corresponding to that in tap water would result in inactivation of the enzyme during the reaction so that the expensive enzyme would be wasted. Thus several mM of a soluble calcium salt such as calcium chloride is usually added for the reaction. However in the case of the preparation of final products such as glucose or isomerized sugars by processing starch, it is necessary to remove the calcium after the reaction, which would significantly increase the work load during the desalting step with an ion exchange resin.

In general, α-amylase has a optimum pH value of 6 or above and few α-amylases would exhibit a high activity in an acidic region. For example, an α-amylase originating from *B. licheniformis* has been known as an acidic α-amylase (cf. Tanaka et al., Japanese Patent Laid-Open No. 151970/1977 and Saito et al., Japanese Patent Laid-Open No. 35083/1973). In a process of liquefying starch, the starch is generally suspended at a concentration of 10 to 30% and then heated. During this step, organic acids contained in the starch material reduce the pH value of the suspension below 5, or frequently below 4. Therefore the suspension is neutralized to a pH value of 6 to 7 by adding slaked lime or calcium carbonate prior to the treatment with α-amylase (cf. Ueno, Japanese Patent Laid-Open No. 19049/1974 and Nakajima et al., Japanese Patent Laid-Open No. 55857/1974).

As described above, glucoamylase is used to hydrolyze the dextrin solution obtained by the above liquefaction into glucose. Since conventional glucoamylase has an optimum pH of 4.5 to 5.0, and acid is further added to acidify the dextrin solution after the neutralization during the liquefying step followed by the hydrolysis. Further neutralization is necessary to separate the produced glucose. Therefore it is necessary to add a neutralizing agent for pH adjustment other than a calcium salt as a protective factor when a conventional thermostable α-amylase is employed, resulting in not only consumption of a reagent but also an additional load in the subsequent desalting step with an ion exchanger. The reaction around neutrality would further bring about the following disadvantages. That is, when the reaction is carried out by heating to a temperature of 80° C. or above, the reduced terminal of a starch molecule would be isomerized, thus causing a decrease in the yield of glucose in saccharification with glucoamylase. In addition, starch would be gelatinized to give a very viscous gel which can be hardly mixed when heated for liquefaction. Under an acidic condition (pH 4), however, the viscosity of the starch gel would fall to approximately 50% of that in a neutral state (pH 6) so that liquefaction in an acidic state is relatively easy.

Up to now, there have been reported no α-amylases available under a condition wherein these requirements are satisfied, i.e. having a very low calcium requirement and a high thermostability and exhibiting a high activity in an acidic region.

SUMMARY OF THE INVENTION

It is an object of the present invention to provide a process for liquefying starch at a low viscosity whereby a load at the desalting step is relieved and the disadvantageous isomerization of reduced terminals is prevented.

In order to improve conventional processes for liquefaction, we have examined various microorganisms for producing enzymes to obtain a novel α-amylases which has a high thermostability and a low calcium requirement and exerts a high activity in an acidic region. As a result, we have found that a thermophilic, anaerobic bacterium belonging to the genus Clostridium (clostridium sp. RS-0001, FERM P-7918) could produce a novel thermostable α-amylases satisfying the above requirements. We have subsequently examined a process for liquefying starch with the use of this α-amylase, thus completing the present invention.

The process of the present invention is characterized in that a raw starch solution can be directly liquefied with a novel thermostable α-amylase according to the present invention in acidic state in the absence of calcium and without adjusting the pH value, which makes unnecessary both the desalting step after the liquefication and the significant pH adjustment when converting the dextrin into glucose with glucoamylase after the liquefaction. This process has further advantages in that the liquefaction mixture can be readily admixed because of a decrease in the viscosity of the raw starch gel.

The starch available in the present invention is not particularly limited. For example, potato starch, sweet potato starch, corn starch, tapioca starch and wheat starch can be used. It is unnecessary to add a calcium salt to sustain the thermostability of the enzyme except that a reagent-class amylose which is mashed with distilled water and calcium is completely removed therefrom. Thus the subsequent desalting step to remove cations becomes needless when ordinary tap water is employed.

No pH adjustment is usually required in the liquefaction since raw starch is contaminated with organic acids which acidify a usual starch solution of a concentration of 10 to 30% (i.e. pH 5 or below). Accordingly the raw starch solution is at an optimum pH value or falls into an appropriate pH range of the novel thermostable α-amylase as such.

The concentration of the raw starch varies depending on the type of starting materials, qualities and usage of the liquefied solution but falls into a conventionally known range of 10 to 40%.

The reaction temperature is 100° C. or below because of the thermostability of the novel thermostable enzyme. Taking into account the reaction rate and thermostability of the enzyme, it is preferable to carry out the reaction at 80° C.

The amount of the enzyme to be added varies depending on the type of the raw starch in the reaction tank and the residence time therein, reaction temperature, pH value and other factors. Once the treatment period is fixed at 0.5 hour, approximately $10^5$ unit/kg of the enzyme is necessary to decompose potato starch into limit dextrins at 80° C. and at pH 4.0. The unit of the α-amylase activity is determined by Blue value method which will be described in detail hereinbelow.

The bacterium (Clostridium sp. RS-001) belonging to the genus Clostridium which produces α-amylase used in the present invention has been deposited with the Fermentation Research Institute of the Agency of Industrial Science and Technology (FERM P-7918). Now mycological properties of this bacterium will be described in detail.

A. Morphological properties (1) Morphology of nutritive cells

A nutritive cell of this bacterium cultured in the starch/peptone medium as will be defined hereinbelow on an agar plate in an anaerobic atmosphere for two days at 60° C. is in the form of a straight rod of 0.4–0.8×2–5 μm in size. After culturing for three days of longer, some nutritive cells are present alone and others are linked with each other. A similar result is observed when cultured in a liquid medium.

| Composition of a starch/peptone medium | |
|---|---|
| soluble starch | 1.5% |
| peptone | 0.5% |
| yeast extract | 0.5% |
| $KH_2PO_4$ | 0.7% |
| $Na_2HPO_4$ | 0.35% |
| $MgSO_4.7H_2O$ | 0.001% |
| agar | 2.0% |
| sodium thioglycolate | 0.1% |
| tap water | g.s. |
| | pH = 6.4 |

(2) Presence of spores

Formation of spores is observed when the bacterium is cultured in the starch/peptone medium on an agar plate or in the liquid medium.

B. Cultivation behaviors (1) Morphology of colonies

A colony obtained by culturing the bacterium in the starch peptone medium on an agar plate is in the form of a fully framed flat circle showing a slight rise at the center. No chromogenesis is observed. It is glossy, milk white, opaque and adhesive.

(2) Similar colonies to those obtained in the starch/peptone medium are formed when the bacterium is cultured in a bouillon medium on an agar plate and stab cultured.

| Composition of a bouillon/agar medium | |
|---|---|
| meat extract | 1.0% |
| peptone | 1.0% |
| common salt | 0.2% |
| sodium thioglycolate | 0.1% |
| agar | 1.5% |
| distilled water | g.s. |
| | pH = 6.0 |

(3) Stab culture in a bouillon medium

It grows with evolving a gas comprising $H_2$ and $CO_2$ so that the agar medium is divided at two or three points.

(4) Culture in a bouillon liquid medium

It grows only under an anaerobic condition and the culturing broth shows self-clouding.

| Composition of a bouillon medium | |
|---|---|
| meat extract | 1.0% |
| peptone | 1.0% |
| common salt | 0.2% |
| sodium thioglycolate | 0.1% |
| distilled water | g.s. |
| | pH = 6.0 |

(5) Culture in a bouillon/gelatin medium

It does not grow.

| Composition of a bouillon/gelatin medium | |
|---|---|
| meat extract | 1.0% |
| peptone | 1.0% |
| common salt | 0.2% |
| gelatin | 15% |
| sodium thioglycolate | 0.1% |
| distilled water | g.s. |
| | pH = 6.0 |

(6) Culture in a litmus milk medium

The medium intimately coagulates with evolving a gas and turns to red by an acid thus formed.

C. Physiological properties (1) Appropriate temperature range for growth

It grows at a temperature of 40° to 63° C. No growth is observed at 30° C. and an excellent growth is observed around 60° C.

(2) Appropriate pH range for growth

It growth in a pH range of 5 to 7. An excellent growth is observed around pH 5.6.

(3) Attitude for oxygen

Obligately anaerobic.

(4) O-F test (Hugh-Laifson variation)

No growth is observed on exposure to air, i.e. negative. It grows when anaerobically cultured by liquid paraffin one-dimentional diffusion method and the acids thus formed turn the culturing broth yellow.

| Composition of a medium | |
|---|---|
| peptone | 0.2% |
| glucose | 1.0% |
| common salt | 0.5% |
| $K_2HPO_4$ | 0.03% |
| sodium thioglycolate | 0.1% |
| bromocresol purple | 0.002% |
| agar | 0.3% |
| distilled water | g.s. |
| | pH = 6.0 |

(5) Reduction of nitrate
Negative.
(6) VP test
Negative.
(7) MR test
It turns red, i.e. positive.
(8) Indole formation
Determination is impossible since it does not grow in aqueous peptone.
(9) Hydrogen sulfide formation
Negative (in a Kligrer medium).
(10) Hydrolysis of starch
Positive. It hydrolyzes not only soluble starch but also granular starch such as potato starch.
(11) Utilization of citric acid
Negative (in a Simmons medium).
(12) Utilization of ammonium salt
Determination is impossible since it does not grow in aqueous peptone.
(13) Extracellular chromogenesis
Negative.
(14) Urease activity
Negative.
(15) Oxidase activity
Negative.
(16) Catalase activity
Negative.
(17) Capability of fermenting sugars
Table 1 shows the capability of fermenting sugars of the bacterium and the presence of evolved gas determined with the use of Durham's tubes.

TABLE 1

| Carbon source | Fermentation | Evolution of gas |
|---|---|---|
| glycerol | − | − |
| D-xylose | + | + |
| D-glucose | + | + |
| D-fructose | + | + |
| D-mannose | + | + |
| D-galactose | + | + |
| L-rhamnose | + | + |
| D-mannitol | + | + |
| D-sorbitol | − | − |
| D-inositol | − | − |
| trehalose | + | + |
| lactose | + | + |
| maltose | + | + |
| sucrose | + | + |
| dextrin | + | + |
| starch | + | + |
| inulin | − | − |
| cellobiose | + | + |

(18) Growth in an inorganic medium
No growth.
(19) Formation of organic acids
Table 2 shows organic acids produced in various media.

TABLE 2

| Main carbon source in medium | Formed organic acid |
|---|---|
| glucose | acetic acid, lactic acid |
| dextrin | acetic acid, lactic acid |
| starch | lactic acid |
| mannitol | lactic acid |
| sucrose | acetic acid, lactic acid |
| maltose | acetic acid, lactic acid |
| rhamnose | acetic acid |

| Composition of a test liquid medium | |
|---|---|
| carbon source | 1.0% |
| peptone | 1.0% |
| common salt | 0.2% |
| sodium thioglycolate | 0.1% |
| distilled water | g.s |
| | pH = 6.4 |

Thus the tested bacterium was identified as one belonging to the genus Clostridium according to Holdeman's manual on classification of anaerobic bacteria.

Now enzymatic properties of the thermostable α-amylase of the present invention will be described.

The α-amylase activity was determined in the following manner.

The dextrinogenic activity was determined according to Blue value method (cf. Jikken Kagaku Koza, ed. by Chem. Suc. Japan, vol. 24, Biochemistry II, p. 279, pub. by Maruzen Co., Ltd., 1969). This method was an application of a theory that the degreee of a blue coloration by a starch/iodine complex would decrease with a decrease in the molecular weight of the starch caused by hydrolysis. 2 ml of a 2 mg/ml starch solution and 1 ml of a 0.1M citrate buffer solution (pH 4.0) were introduced into a test tube and shaken in a water bath at 60° C. for five min. Then 1 ml of a culturing filtrate was added thereto as a crude enzyme solution and the mixture was allowed to react for 30 min. After the completion of the reaction, 0.4 ml of the reaction mixture was collected and immediately mixed with 2 ml of a 0.5M acetic acid solution to thereby stop the enzymeatic reaction. Then 1 ml of the mixture was added to 10 ml of a 1/3000N iodine solution and the optical density was determined at 680 nm with a spectrometer. Separately the reaction mixture immediately after the addition of the enzyme solution was collected to develop the color in a similar manner. The optical density thereof was also determined. An amylose of a degree of polymerization of approximately 2000 was employed as the starch.

The α-amylase activity was calculated by the following equation:

$$\alpha\text{-amylase activity (u)} = \frac{O.D.\text{-at 0 time} - O.D.\text{ after reacting for 30 min}}{O.D.\text{ at 0 time}} \times 10$$

(1) Action and substrate specificity
This enzyme is a liquid α-amylase which hydrolyzes potato starch, corn starch, sweet potato starch etc.
(2) Optimum pH
FIG. 1 shows curves representing changes in the α-amylase activity of a typical known α-amylase with pH. Curve 5 shows that according to Japanese Patent Laid-Open No. 12946/1971. An α-amylase originating from Bacillus subtilis (cf. Ogasawara et al., J. Biochem., 67, 65 (1970)) as shown by curve 4 and that originating from *B. licheniformis* (cf. Saito et al., Japanese Patent Laid-Open No. 35083/1973) as shown by curve 5 have each an appropriate pH region of 4 to 11 (a pH region wherein the corresponding enzyme exhibits an activity as high as 80% of that at the optimum pH value). An α-amylase originating from *B. licheniformis* (cf. Tanaka et al., Japanese Patent Laid-Open No. 151970/1977), which exhibits the highest activity in an acidic region among known acidic α-amylases, has an appropriate pH range of 3.5 to 6.3 and exhibits no activity at pH 2.

In contrast to these enzymes, α-amylases I and II of the present invention as shown by curves 1 and 2, respectively, have each an optimum pH range around 4. Appropriate pH values thereof are 2 to 5.7 and 2 to 6.3, respectively. Thus these α-amylases exhibit higher activities in an acidic region than conventional ones. That is, the α-amylases of the present invention exhibit activities as high as 95% and 81% at pH 2, while conventional acidic α-amylases exhibit no activity.

The following reaction system was employed in the enzymatic reaction:

| enzyme solution | 0.6 to 1.3 μg/ml, |
| substrate | amylose 1 mg/ml, and |
| citrate buffer solution | 0.025 M. |

As described above, the α-amylases of the present invention has an appropriate pH range different from those of conventional acidic α-amylases, which clearly suggests that the former is a novel α-amylase.

(3) pH stability

The α-amylases I and II used in the present invention were incubated at pH 2, 4, 6 and 7 (in a 0.025M citrate buffer solution) at 60° C. for 30 min. Each reaction solution was diluted and adjusted to a pH value of 4. The residual activity was determined by using amylose as a substrate. Consequently it was found that both α-amylases fully sustained their activities by the above treatment, which suggests that these α-amylases are characterized in that they are stable in an acidic region.

(4) Optimum temperature

As shown in FIG. 2, the α-amylases I and II of the present invention corresponding to curves 11 and 12, respectively, have each an optimum temperature around 80° C., at pH 4.0. An appropriate temperature range of each α-amylase wherein the enzyme would exhibit an activity as high as 80% of that at the optimum temperature is 65° to 87° C. A 0.025M citrate buffer solution was employed in the determination.

(5) Thermostability

The α-amylase II used in the present invention was heated to 60° to 97° C. at pH 6.0 in the presence of 20 μM of calcium chloride and the residual activity was determined. Based on the data thus obtained a half-life period of the activity at each temperature was determined. FIG. 3 shows the result. Half-time periods of the activity at 80° C. and 90° C. without any substrates are eight hours and 0.5 hour, respectively, which suggests that the α-amylase II is stable to heat. Similarly the α-amylase I show a half-life period of approximately 0.5 hour at 90° C. On the other hand, two partially purified α-amylase specimens prepared from culturing brothes of an α-amylase producing a strain belonging to *B. licheniformis* and that belonging to *B. subtilus*, respectively, were employed as examples of conventional α-amylases. The half-life period of each specimen was determined at a calcium concentration of 20 mM. FIG. 3 further shows the result. The determination was performed with the use of a citrate buffer solution at pH 6.0 which was an optimum pH value of each α-amylase. The half-life period of the former α-amylase at 80° C. is 0.6 hour, while that of the latter α-amylase at 70° C. is 0.6 hour. The thermostability of the α-amylase used in the present invention (curve 21) is lower than those of conventionally known thermostable α-amylases belonging to the genus Thermus, but similar to that of a thermostable α-amylase originating from *B. licheniformis* (curve 22).

(6) Effect of metal salts on thermostability

Table 3 shows effects of various metal salts on the thermostability of the α-amylase II used in the present invention. Each metal salt was added to an aqueous solution of the α-amylase II to give a concentration of 5 mM. The activity of the obtained mixture was determined before and after heating. The residual activity (i.e. activity after heating/activity before heating) is represented in %. The heat treatment was carried out under the following conditions:

| pH | 6.0 |
| temperature | 80° C. |
| period | 30 min. |

TABLE 3

| Added metal salt (5 mM) | Residual activity (%) |
| --- | --- |
| sodium chloride | 79 |
| potassium chloride | 54 |
| magnesium chloride | 50 |
| calcium chloride | 100 |
| manganese chloride | 15 |
| nickel chloride | <1 |
| cobalt chloride | <1 |
| zinc chloride | <1 |
| none | 60 |

The activity was determined under the following condition after diluting the sample. The result indicates that the activity of this enzyme is not affected by the addition of each metal salt at the above concentration.

| Activity determination | |
| --- | --- |
| pH | 4.0 (in 0.025 M citrate buffer solution) |
| temperature | 60° C. |

Table 3 clearly shows that calcium ion exerts a protective effect while sodium, potassium, and magnesium ions exert little effects. On the other hand, nickel, cobalt, zinc and manganese ions lower the thermostability. It is further confirmed that this α-amylase lose its thermostability by adding 0.5 μM of EDTA.

The calcium concentration required by this α-amylase is 100 μM (4 ppm) as shown by curve 31 in FIG. 4, so that it is sufficiently stabilized at the calcium concentration in tap water. Further this enzyme sustains 64% of the activity at a calcium concentration below 1 μM. The α-amylase I shows a calcium requirement similar to that of the α-amylase II.

In contrast, an α-amylase prepared by partially purifying an α-amylase producing strain of *B. licheniformis* requires 30 mM of calcium ion as shown by curve 32 in FIG. 4. Each enzyme was heated to 80° C. at pH 6.0 for 30 min and the activity was determined at the optimum pH value thereof at 60° C.

A thermostable α-amylase originating from *B. subtilis* requires calcium at a concentration of 3 to 10 mM (cf. Japanese Patent Laid-Open No. 44690/1976 and No. 34117/1983).

Thus the calcium requirement of the α-amylase of the present invention is significantly lower than those of known thermostable α-amylases.

(7) Purification

A process for the purification of this enzyme will be briefly described here, because it will be described in detail in Examples hereinbelow.

A strain capable of producing the α-amylase used in the present invention is inoculated into a liquid medium containing starch, peptone and yeast extract and anaerobically cultured therein at 60° C. for one to three days. The culturing broth is centrifuged to remove cells and other insoluble matters, thus giving a so-called culturing filtrate. The culturing filtrate is then purified by an appropriate method such as molecular sieve membrane filtration, ion exchange chromatography, gel filtration chromatography or salting out to thereby concentrate the α-amylase of the present invention and to remove impurities.

(8) Molecular weight

Though the molecular weight of the α-amylase of the present invention has not yet been determined, its behavior during molecular sieve membrane filtration suggests that it may have a molecular weight of 20,000 or above.

These facts as described above clearly show that the thermostable α-amylase used in the present invention is significantly different from conventional thermostable enzymes produced by anaerobic bacteria, in particular in its working pH range and calcium requirement.

DETAILED DESCRIPTION OF PREFERRED EMBODIMENTS

EXAMPLE 1

4.56 kg of a liquid medium (pH 6.4) comprising 1.5% of soluble starch, 0.5% of polypeptone, 0.5% of yeast extract, 0.7% of potassium phosphate, 0.35% of disodium phosphate, 0.01% of magnesium sulfate heptahydrate, 0.1% of sodium thioglycolate and an appropriate amount of tap water was prepared. 1.52 kg portions of this medium were introduced into three fermentation tanks of 5 l in volume and sterilized at 120° C. for 20 min. 80 g of a suspension of a bacterium belonging to the genus Clostridium which had been isolated by us and anaerobically cultured in the above medium was added to each tank. A water seal trap was attached to the gas outlet of the tank and the gas phase in the tank was sufficiently purged with argon gas. Then the bacterium was anaerobically cultured therein. The pH value and temperature of the medium was automatically adjusted to 6.0 and 60° C., respectively. After culturing for 46 hours, the culturing broths were combined and centrifuged at 6,000 rpm to remove cells. The supernatant thus obtained showed a specific activity of 49 unit/g.

Figure 5:
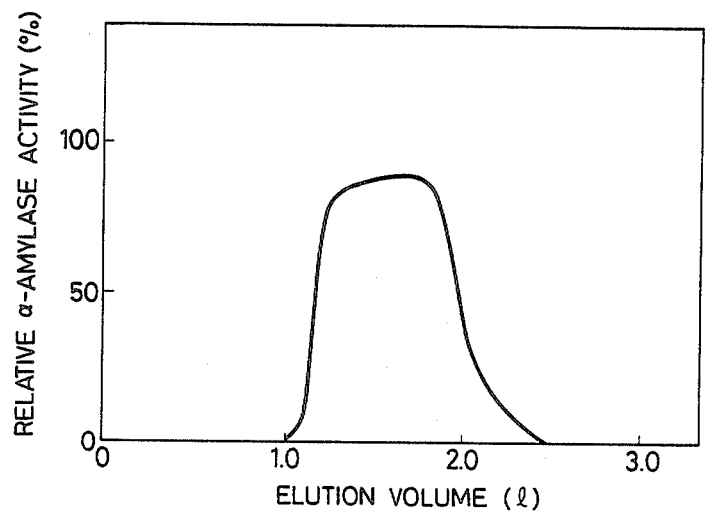
FIG. 5 shows an elution pattern of the α-amylase activity of the thermostable α-amylase obtained by molecular sieve liquid chromatography.

Subsequently 3.5 kg of the above supernatant was filtered through a molecular sieve membrane (fractionation molecular weight: 20000) to thereby concentrate the same to 1.5 kg. The concentrate was divided into halves. 0.75 kg of the concentrate was charged into a column ($\phi$100 mm $\times$ 450 mm) of a crosslinked dextran gel (fractionation molecular weight: 2500, mfd. by Pharmacia AB) to subject it to molecular sieve liquid chromatography. FIG. 5 shows an elution pattern of the α-amylase activity thus determined. The elution was carried out in deionized water and the eluate was fractionated in 100 ml portions. As shown in FIG. 5, fractions of 1.2 to 2 l show the α-amylase activity. The residual supernatent was also subjected to the same liquid chromatography as described above. Both α-amylase fractions were combined and lyophilized in vacuo (40 Torr) to give 2.7 g of a crude dry powder.

The crude specimen of this enzyme showed a specific activity of 39000 unit/g which was approximately 800 times as high as that of the supernatant. The activity yield is approximately 60%.

Example 2

Figure 6:
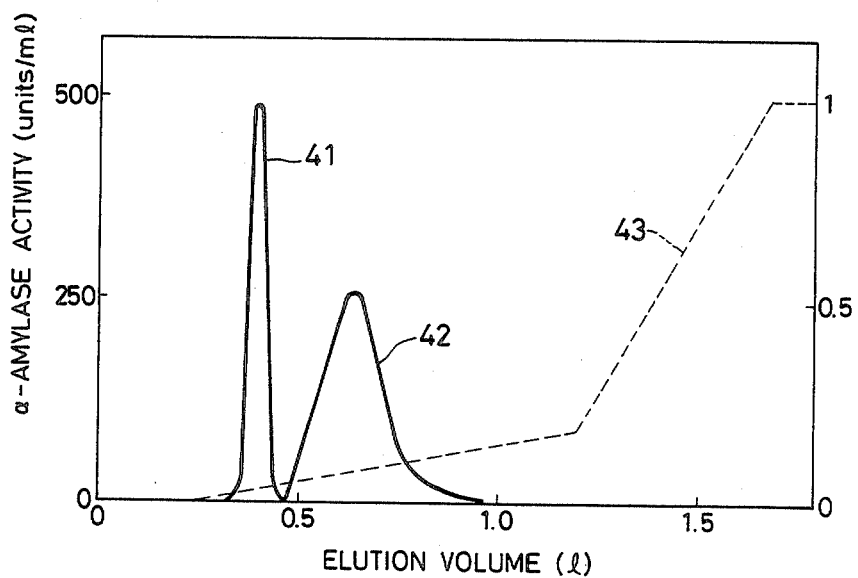
FIG. 6 shows an elution pattern of the α-amylase activity of the thermostable α-amylase used in the present invention obtained by ion exchange liquid chromatography with the use of a diethylaminoethylated, crosslinked dextran gel.

The crude enzyme specimen prepared in Example 1 was purified by ion exchange chromatography with the use of a diethylaminoethylated crosslinked dextran gel (DEAE Sepharose; mfd. by Pharmacia AB; column size: $\phi$25 $\times$ 400 mm). 2.4 g of the dry crude enzyme specimen was dissolved in a 0.05M Tris hydrochloride buffer solution (pH 7.5). After removing insoluble matters by filtration, the filtrate was charged in a gel column equilibrated with the same buffer solution and washed. Then it was developed with increasing the concentration of the sodium chloride in the buffer solution with a linear gradient (curve 43). FIG. 6 shows the elution pattern of the α-amylase activity. Two peaks indicating the α-amylase activity are observed with sodium chloride concentrations of 0.04M and 0.08M. Curves 41 and 42 correspond to α-amylase I and α-amylase II, respectively. The active fraction of the α-amylase I is approximately 30% of the total adsorbed activity while that of the α-amylase II is 60% thereof. The specific activity of the α-amylase I prepared by lyophilizing the corresponding fraction is 390 unit/mg while that of the α-amylase II is 880 unit/mg. These specific activities are respectively 10 times and 20 times as high as that of the crude dry enzyme specimen. The activity yields of the culturing broth based on the centrifuged supernatant are 19% and 35%, respectively.

Subsequently potato starch was liquefied with the α-amylase II as prepared above.

1.5 g of potato starch was suspended in 5 ml of distilled water. The pH value of the starch suspension was 4.5. 750 units of the α-amylase II was added thereto and the mixture was maintained in a water bath at 90° C. with slowly stirring. The liquefied solution was collected and diluted with distilled water. This solution showed no coloration in iodine reaction, which indicated that the liquefaction was completed. The calcium concentration in the liquefied solution determined by atomic absorption spectroscopy was 2.1 μM.

Comparative Example 1

Figure 1:
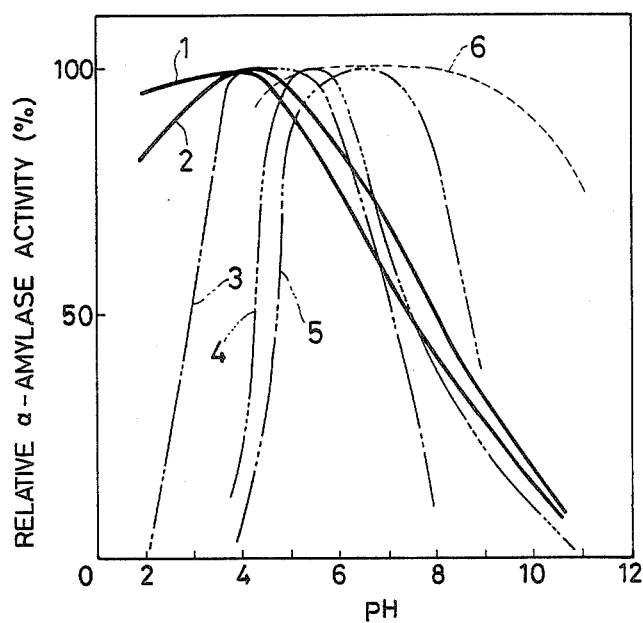
FIG. 1 shows an effect of pH on the α-amylase (i.e. dextrinogenic) activities of the thermostable α-amylases used in the present invention and those of conventional thermostable α-amylases.
Figure 2:
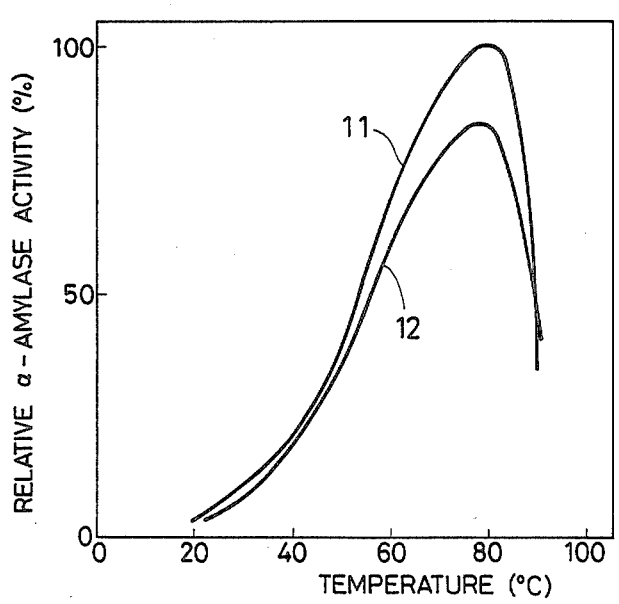
FIG. 2 shows an effect of temperature on the α-amylase activities of the thermostable α-amylases used in the present invention.
Figure 3:
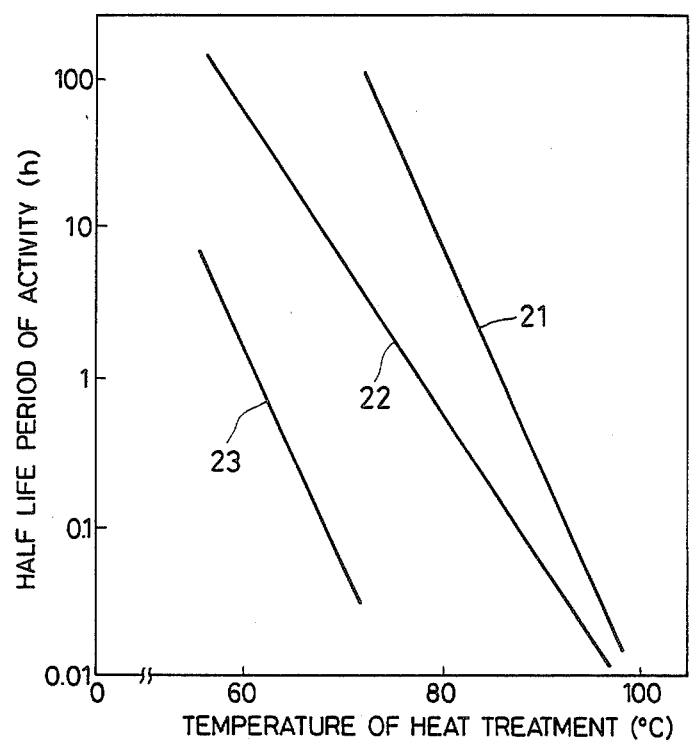
FIG. 3 shows thermostabilities of the thermostable α-amylases used in the present invention and those of conventional thermostable α-amylases in the above Examples.
Figure 4:
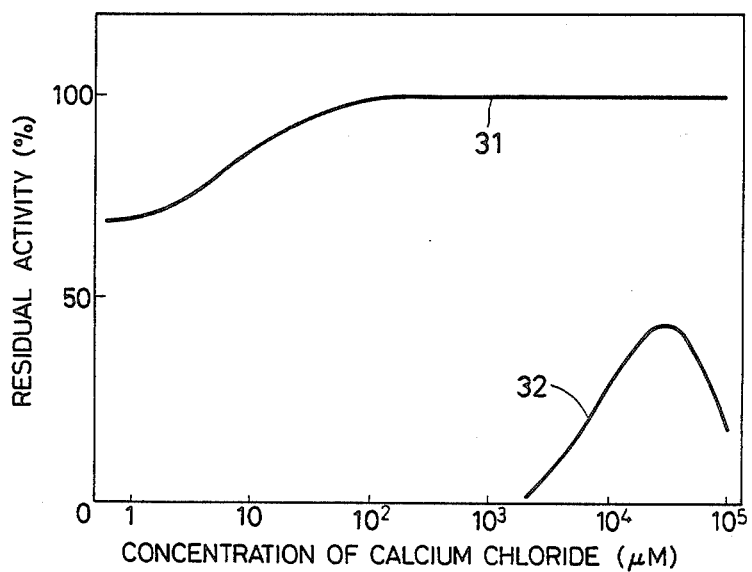
FIG. 4 shows an effect of calcium concentration on the α-amylase activities of the thermostable α-amylases used in the present invention and those of conventional thermostable α-amylases both previously heated in the above Examples.

Potato starch was liquefied in the same manner as described in Example 2 except that a thermostable α-amylase originating from *B. licheniformis* was employed as an example of conventional thermostable α-amylases as shown in FIGS. 3 and 4. The liquefied solution was collected and diluted. The solution showed a dark blue coloration when reacted with iodine. The rate of hydrolysis as determined by colorimetry was 5.1%.

Comparative Example 2

1.5 g of potato starch of the same lot as used in Example 2 was suspended in 4 ml of distilled water and 0.1 ml of a 1N caustic soda solution was added thereto to give a pH value of 6.0. 750 units of the thermostable α-amylase originating from *B. licheniformis* of the same lot as used in Comparative Example 1 was added thereto and additional distilled water was added to give a total volume of 5 ml. After liquefying the mixture in the same manner as described in Comparative Example 1, the rate of hydrolysis as determined by colorimetry was 12%.

Comparative Example 3

1.5 g of potato starch of the same lot as used in Example 2 was suspended in 4 ml of distilled water. Then calcium chloride was added to give a final concentration of 50 mM. A 1N caustic soda solution was further added to adjust the pH value to 6.0 and additional distilled water was added to give a total volume of 5 ml. 750 units of the thermostable α-amylase originating from *B. licheniformis* of the same lot as used in Comparative Example 1 was added thereto. The rate of hydrolysis as determined in the same manner as described in Comparative Example 1 was 42%.

Comparative Example 4

Potato starch was liquefied in the same manner as described in Comparative Example 1 except that a mesophilic α-amylase originating from *B. subtilus* as shown in FIG. 3 for comparison was employed and the pH value was adjusted to the optimum pH value of the enzyme (i.e. 6.0). The rate of hydrolysis was 4.0%.

Comparative Example 5

Potato starch was liquefied with the mesophilic α-amylase originating from *B. subtilus* as shown in FIG. 3 in the same manner as described in Comparative Example 4 except that calcium chloride was added to give a final concentration of 10 mM simultaneously with the adjustment of the pH value to 6.0. The rate of hydrolysis was 5.1%.

Example 3

4 g of corn starch was suspended in 10 ml of tap water. The pH value of the obtained suspension was 4.0. Separately 5 ml of distilled water in a 50 ml beaker was immersed in a water bath at 80° C. and 500 units of α-amylase I was added thereto. Subsequently the above starch solution was added dropwise to the liquor in the beaker with stirring within 10 min and the mixture was maintained at 80° C. for 50 min. The solution thus liquefied was collected. The rate of hydrolysis thereof was 94%.

Example 4

4 g of the corn starch of the same lot as used in Example 3 was subspended in 10 ml of tap water. The above suspension was heated in an autoclave at 120° C. for 30 min to thereby cause gelation. Separately 500 units of α-amylase II was added to 5 ml of distilled water in a 50 ml beaker in a water bath at 80° C. The starch gel was added in portions thereto with stirring within 10 min. The mixture was maintained at the same temperature for additional 50 min. The liquefied solution was collected and diluted. The rate of hydrolysis thereof was 98%.

In the process of the present invention, it is unnecessary to add a calcium salt in liquefying starch and the starch slurry can be reacted while remaining acidic without neutralization, so that the load at the desalting step of the product can be significantly relieved.

We claim:

1. A process for liquefying starch which comprises contacting α-amylase obtained by culturing of Clostridium sp. RS-0001, FERM P-7918, with an aqueous slurry or solution of the starch at an elevated temperature at a pH value of 5.5 or lower and at a calcium ion concentration of 100 μM or lower.

2. A process for liquefying starch according to claim 1, wherein the starch is liquefied without adding any calcium salts to the liquefying slurry or solution.

3. A process for liquefying starch according to claim 1, wherein the elevated temperature is not more than 100° C.

4. A process according to claim 1, wherein the elevated temperature is from 80° to 100° C.

5. A process for liquefying starch according to claim 1, wherein the calcium ion concentration is 10 μM or below.

6. A process for liquefying starch according to claim 1, wherein the calcium concentration is 1 μM or below.

* * * * *